United States Patent [19]

Herr et al.

[11] 4,009,283
[45] Feb. 22, 1977

[54] ANTIINFLAMMATORY AND ANTITHROMBOTIC COMPOSITIONS AND METHOD OF USE

[75] Inventors: Milton E. Herr, Deltona, Fla.; Roy A. Johnson, Kalamazoo, Mich.

[73] Assignee: The Upjohn Company, Kalamazoo, Mich.

[22] Filed: Feb. 6, 1976

[21] Appl. No.: 655,897

Related U.S. Application Data

[62] Division of Ser. No. 413,647, Nov. 7, 1973, Pat. No. 3,957,861.

[52] U.S. Cl. .............................. 424/317; 424/308
[51] Int. Cl.² ............... A61K 31/19; A61K 31/235
[58] Field of Search ........................... 424/317, 308

*Primary Examiner*—Stanley J. Friedman
*Attorney, Agent, or Firm*—Martin B. Barancik; Roman Saliwanchik

[57] ABSTRACT

In accordance with this invention, there are disclosed compounds of the formula

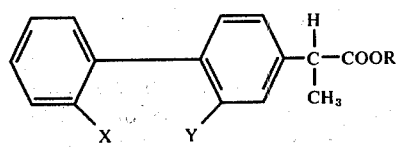

wherein X is selected from the group consisting of nitro and amino with the proviso that when Y is hydrogen, X is nitro; Y is selected from the group consisting of hydrogen and fluoro; R is selected from the group consisting of hydrogen and alkyl of from one to six carbon atoms, inclusive.

These compounds are compounded into pharmaceutical compositions and administered to mammals for purposes of relieving inflammation and to mammals in need of prophylactic anti-thrombotic treatment.

12 Claims, No Drawings

ANTIINFLAMMATORY AND ANTITHROMBOTIC COMPOSITIONS AND METHOD OF USE

CROSS REFERENCE TO RELATED APPLICATIONS

This is a divisional application of pending application Ser. No. 413,647, filed Nov. 7, 1973 and now issued as U.S. Pat. No. 3,957,861.

BRIEF DESCRIPTION OF THE PRIOR ART

Non-steroidal anti-inflammatories are well known in the art. U.S. Pat. No. 3,624,142 discloses in its generic formulae a very large number of substituted and unsubstituted biphenyl acetic, higher alkyl acids, and esters thereof. In British Patent No. 1,091,403, structural formulae of similar scope as the above patent, but with preferred subgenera substituted in the 2 and 2' positions of the biphenyl moiety, are disclosed. There have been a number of recent papers which show that certain tested non-steroidal anti-inflammatories also have anti-thrombotic activity.

In the treatment of various conditions affecting mammals of higher order, including humans, it can be very beneficial to have splits in various biological activities, that is, one activity at a given dosage being significantly higher or lower than a second biological activity. This is clearly the case where anti-inflammatory and anti-thrombotic biological activities are involved. The term "anti-thrombotic", as used throughout this specification and appended claims, refers to the inhibition of blood platelet aggregation. Platelet aggregation can be an intermediate of full fibrinogen related clots and, in and of itself, platelet aggregation appears to cause mortality in some cases.

Aside from the fact that anti-thrombotic activity may be associated with the stomach bleeding and ulcerative effects of a large number of non-steroidal anti-inflammatories, significant splits in activity are art recognized as important in certain areas. For example, some people suffering from inflammatory conditions such as arthritis and osteomyelitis, also may be suffering from hemophelia, leukemia, or aplastic anemia, all conditions which affect the clotting time of blood. Under these circumstances, a drug having relatively high anti-inflammatory activity and relatively low anti-thrombotic activity is clearly beneficial. In the other extreme, there are situations where a drug with high anti-thrombotic activity and low anti-inflammatory activity is a distinct advantage. For example, following surgery, particularly cardiovascular surgery, the administration of a compound which can prevent post-operative thrombosis is clearly advantageous. However, if one has a tendency to stomach ulcers, a drug with anti-inflammatory activity would not be beneficial to that condition. Consequently, a drug with high anti-thrombotic and low anti-inflammatory activity is of great benefit in situations of like circumstances.

Certain compounds which show these significant splits in activity have been discovered.

BRIEF DESCRIPTION OF THE INVENTION

In accordance with this invention, there are disclosed compounds of the formula

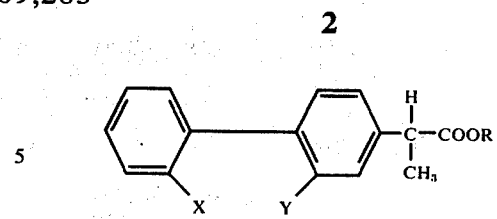

wherein X is selected from the group consisting of nitro and amino with the proviso that when Y is hydrogen, X is nitro; Y is selected from the group consisting of hydrogen and fluoro; R is selected from the group consisting of hydrogen and alkyl of from one to six carbon atoms, inclusive.

These compounds are compounded into pharmaceutical compositions and administered to mammals for purposes of relieving inflammation and to mammals in need of prophylactic anti-thrombotic treatment.

DETAILED DESCRIPTION OF THE INVENTION

The compounds of this invention are prepared by conventional synthetic procedures known to the art. For example, 2-(2-fluoro-4-biphenylyl)propionic acid is nitrated with nitric acid to give the 2' and 4' nitroisomers, the methyl esters are prepared with diazomethane and the isomeric nitro esters, separated by chromatography, are hydrolyzed to the respective acids. The 2-(2-fluoro-2'-nitro-4-biphenylyl)propionic acid is then readily reduced to the 2'-amino analogue by catalytic hydrogenation.

The 2-(2'-nitro-4-biphenylyl)propionic acid is readily prepared in the following manner: 2-nitrobiphenyl is acylated with acetyl chloride, giving 4-acetyl-2'-nitrobiphenyl. This is converted with chloroacetonitrile under alkaline conditions to the intermediate isomeric 2-methyl-2-[4-(2'-nitrophenyl)]glycidonitriles which, when treated with lithium perchlorate and then base, is isomerized to methyl 2-(2'-nitro-4-biphenylyl)propionate. Saponificiation of the latter gives the desired 2-(2'-nitro-4-biphenylyl)propionic acid. The esters are readily converted to the acid and the acid to the esters by conventional means.

As used in the specification, alkyl of one to six carbon atoms, inclusive, includes methyl, ethyl, propyl, butyl, pentyl, hexyl, and isomers thereof.

The compounds of Formula 1 have an asymmetric carbon atom at carbon 2 and can exist as optical isomers. For the purpose of this invention, the racemic mixtures and dextro forms are active. The levo form is essentially inactive.

The compositions of the present invention are presented for administration to humans and animals in unit dosage forms, such as tablets, capsules, pills, powders, granules, sterile parenteral solutions or suspensions, rectal suppositories, oral solutions or suspensions, oil-in-water and water-in-oil emulsions and for anti-inflammatory effects, topical compositions such as lotions, creams, sprays, and the like containing suitable quantities of the compound of Formula 1.

For oral administration either solid or fluid unit dosage forms can be prepared. For preparing solid compositions such as tablets, the compound of Formula 1 is mixed with conventional ingredients such as talc, magnesium stearate, dicalcium phosphate, magnesium aluminum silicate, calcium sulfate, starch, lactose, acacia, methylcellulose and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The oil soluble forms can be dissolved in a vehicle such as corn oil or peanut oil, together with sugar, aromatic flavoring agents and preservatives to form a fluid preparation. Additionally, water and a suitable surfactant may be added to form a syrup. An elixir is prepared by using a hydro-alcoholic (ethanol) vehicle with suitable sweeteners such as sugar and saccharin, together with an aromatic flavoring agent.

Suspensions can be prepared with an aqueous or oil vehicle with the aid of a suspending agent such as acacia, tragacanth, methylcellulose and the like.

For parenteral administration, fluid unit dosage forms are prepared utilizing the compound and a sterile vehicle, water, corn oil, peanut oil, or other acceptable non-aqueous vehicle. The compound, depending on the vehicle and concentration used, can be either suspended or dissolved in the vehicle. In preparing solutions, the compound can be dissolved in corn oil or peanut oil for injection and filter sterilized before filling into a suitable vial or ampul and sealing. Advantageously, adjuvants such as a local anesthetic, preservative and buffering agents can be dissolved in the vehicle. Parenteral suspensions are prepared in substantially the same manner except that the compound is suspended in the vehicle, preferably water, instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

A rectal suppository can be employed to deliver the active compound where the mammal cannot be treated conveniently by means of other dosage forms, such as orally, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weight from about 1 to 2.5 gm.

For topical use as an anti-inflammatory the compounds can be formulated in a pharmaceutical carrier suitable for application to affected areas of the skin, eyes or ears. Accordingly, the compositions of this invention include those pharmaceutical forms in which the medication is applied externally for contact with the area to be treated. Conventional pharmaceutical forms for this purpose include ointments, creams, lotions, solutions, suspensions, pastes, jellies, sprays and aerosols (e.g., for oral or nasal use or on the skin), drops, suppositories, powders (e.g., for use on the skin) and the like. In preparing the desired topical formulations of the novel compound of this invention, various additives, solvents, diluents and adjuvants can be utilized. These illustratively include water, surfactants (e.g., polysorbate 80 and polyoxyethylene sorbitan monostearate), emulsifiers (e.g., glyceryl monostearate-diethylaminoethyl alkyl amide phosphate, isopropyl myristate and cetyl alcohol), alcohols (e.g., ethanol and isopropanol), lower alkyl diols (e.g., 1,3-butanediol, 2,3-butanediol, 1,2-propanediol, 1,3-propanediol), glycols (e.g., propylene glycol, glycerol, sorbitol), ointment-type bases (e.g., spermaceti, Carbowaxes, beeswax, petrolatum, lanolin), higher fatty acids and alcohols (e.g., stearic acid, stearyl alcohol, cetyl alcohol, palmitic acid), liquid paraffin and vegetable oils (e.g., peanut oil, castor oil), preservatives such as sorbic acid, parabens, chlorocresol, benzalkonium chloride) and solid diluents (e.g., lactose, starch, bentonite, talc).

The dosage for mammals varies according to the condition, weight and other parameters of the particular subject being dosed. Generally, a dosage of from about 5 to about 500 mg. per oral or rectal dose administered one to three times daily will bring about a satisfactory anti-inflammatory response when X is nitro and Y is fluoro. Expressed in terms of weight, the dose can be from about 0.1 to about 30 mg./kg. day. The preferred dose is from about 25 to about 150 mg. orally or rectally, one to three times a day for an adult human. When administered parenterally, the dose is from about 10 to about 50 mg., administered intramuscularly, one to two times daily to an adult human.

When administered topically, the compound should be one to fifteen weight percent, preferably five to ten weight percent of the composition.

When X is nitro and Y is hydrogen or X is amino and Y is fluoro, the dosing to obtain an anti-thrombotic effect with either compound in a mammal is the oral or rectal administration of from about 1 to about 100 mg. one to three times daily. Expressed in terms of weight, the dose can be from about 0.02 to about 10 mg./kg./day. The preferred dose is from about 5 to about 50 mg. one to three times daily, administered orally or rectally, to an adult human. When administered parenterally, the dose is from about 10 to about 50 mg. intramuscularly one to two times daily to an adult human.

The disclosure below is of specific examples of this invention. These examples are not intended to limit the broad invention disclosed but merely to exemplify this invention.

EXAMPLE 1

2-(2-Fluoro-2'-nitro-4-biphenyl)propionic acid

A mixture of 50.0 g. of 2-(2-fluoro-4-biphenylyl)propionic acid and 850 ml. of 70% nitric acid is stirred with an efficient air stirrer. The suspended solid gradually goes into solution during the first two hours. The reaction is continued for a total of 165 minutes after which thin layer chromatography indicates complete reaction to two major products. The reaction mixture is then poured onto 2 kg. of ice. When the ice is melted the mixture is extracted four times with methylene chloride. The combined extracts are washed with water and dried over sodium sulfate. Evaporation of the solvent leaves the nitrated products as an orange gum. The nitrated products are taken up in 123 ml. of ethylene dichloride, treated with 50 ml. of methanol and 6.2 ml. of concentrated sulfuric acid and are heated at reflux for 3.5 hours. The mixture is cooled, diluted with 500 ml. of methylene chloride and the organic layer is washed twice with water, once with aqueous sodium bicarbonate, and finally with water, and dried ($Na_2$-

$SO_4$). The residue from concentration of the organic solution is chromatographed on silica gel (packed as a slurry with 10% acetone in Skellysolve B). In this way there is obtained first, 24.80 g. of methyl 2-(2-fluoro-4'-nitro-4-bihenylyl)propionate and second 27.60 g. of methyl 2-(2-fluoro-2'-nitro-4-biphenyl)propionate from elution of the column with 10% acetone in Skellysolve B.

8.5 g. of methyl 2-(2-fluoro-2'-nitro-biphenylyl)propionate dissolved in 180 ml. of methanol is treated with 36 ml. of 10% aqueous sodium hydroxide solution at reflux temperature for one hour. The mixture is concentrated to remove most of the methanol, chilled and acidified with a mixture of 50 ml. of concentrated HCl and 50 g. of ice. The mixture is extracted four times with methylene chloride, the extract washed with water and dried ($Na_2SO_4$). Following removal of solvent, the residue crystallizes and is decolorized with activated carbon and crystallized from ether-pentane. 2-(2-fluoro-2'-nitro-4-biphenylyl)propionic acid crystallizes. m.p. 106°–108°.

nmr ($COCl_3$) 1.50 (doublet, 3H, $—CHCH_3$); 3.77 (quartet. 1H, $—CHCH_3$); 6.92–8.1 (multiplet, 7H, phenyl); 11.68 (singlet, 1H, —COOH).

Analysis Calcd. for: $C_{15}H_{12}FNO_4$; C, 62.28; H, 4.18; N, 4.84; F, 6.57; Found: C, 62.26; H, 4.14; N, 4.67; F, 7.11

This compound is high in anti-inflammatory activity and low in anti-thrombotic activity.

EXAMPLE 2

2-(2-Fluoro-2'-amino-4-biphenylyl) propionic acid 1.58 g. of the methyl ester of 2-(2-fluoro-2'-nitro-4-biphenylyl)propionic acid in 100 ml. of ethanol is treated with 300 mg. of 5% Pd on carbon and shaken with hydrogen (50 psig.) for 35 minutes. The catalyst and solvent are removed. The residue is taken up in ether and treated with one equivalent of ethereal HCl. The HCl salt is recovered and washed with ether. The yield is 1.08 g. The sample obtained from acetone-ether melts at 186°–196°.

Analysis Calcd. for: $C_{16}H_{17}ClFNO_2$: C, 62.03; H, 5.53; N, 4.52; F, 6.13; Found: C, 61.82; H, 5.51; N, 4.60; F. 6.21

0.85 g. of the methyl ester hydrochloride of 2-(2-fluoro-2'-amino-4-biphenylyl)propionic acid in 3 ml. of methanol is treated with 1 ml. of 10% aqueous sodium hydroxide at 27° for 30 minutes. The pH is carefully adjusted to 7 with dilute HCl; part of the methanol is evaporated and water added to crystallize the product. This is recovered by filtration, washed with water and dried: yield 0.385 g., melting point 133°–134°.

Analysis Calcd for: $C_{12}H_{14}FNO_2$: C, 69.48; H, 5.44; N, 5.40; F, 7.33; Found: C, 68.95; H, 5.41; N, 5.58; F, 7.80

This compound is high in anti-thrombotic activity and low in anti-inflammatory activity.

EXAMPLE 3

2-(2'-Nitro-4-biphenylyl)propionic acid a. 4-Acetyl-2'-nitrobiphenyl

A suspension of 96.0 g. of aluminum chloride and 135 ml. of methylene chloride is stirred and treated with a mixture of 60 ml. of methylene chloride, 63 ml. of acetyl chloride, and 77.4 g. of 2-nitrobiphenyl. The mixture is heated at reflux for three hours and cautiously poured into 1200 g. of ice and 900 ml. of concentrated hydrochloric acid. The mixture is extracted with methylene chloride. The extract is washed with water and aqueous sodium bicarbonate, dried ($Na_2SO_4$), and the solvent removed to give a dark oil. This is stirred with 200 ml. of ether and the resulting solid recovered and washed with 1:1 ether:Skellysolve B; yield 53.50 g., m.p. 106°–109°. For analysis a sample is recrystallized from ether; m.p. 108°–111°.

b. Cis and Trans 2-methyl-2-[4-(2'-nitrobiphenyl)]-glycidylnitrile 12.3 g. of crushed sodium hydroxide pellets, 4 ml. of dimethylformamide, and 20.73 g. of 4-acetyl-2'-nitrobiphenyl is stirred under nitrogen and treated with 9.60 g. of chloroacetonitrile in 25 ml. of toluene during sixty minutes, while maintaining the temperature at 17°–19°. The reaction mixture is then stirred with no temperature control for two hours and treated with 1.5 g. of celite, 30 ml. of ether, and 50 ml. of water. This mixture is filtered through a pad of celite and the cake washed with 100 ml. of ether. The layers from the combined filtrate and wash are separated and the top organic solution washed twice with water and dried ($Na_2SO_4$). This dried organic solution is stirred with 5.0 g. of Norite (activated carbon) filtered through celite and the cake washed with 200 ml. of ether. The solvent is removed from the filtrate to leave a straw colored oil, 19.4 g. Nmr analysis indicates the ratio of cis to trans isomers is about 1.2 and also 8–10% of toluene remains.

c. Methyl 2-(2'-nitro-4-biphenylyl)propionate

A mixture of 19.0 g. of the above described glycidylnitrile, 18 ml. of Skellysolve B, and 0.7 g. of lithium perchlorate is stirred and heated under nitrogen reflux for sixteen hours. The mixture is allowed to cool slightly, diluted with 50 ml. of toluene, and treated with 18 ml. of water and 14 ml. of 50% aqueous sodium hydroxide solution, stirred and heated under nitrogen at 70°–75°for six hours. The mixture is cooled, diluted with water, the layers separated and the aqueous layer extracted three times with ether. The alkaline aqueous layer is acidified with a mixture of 50 ml. of concentrated hydrochloric acid and ice and is extracted with methylene chloride. The extract is washed with water and dried, and the solvent removed to give 17.1 g. of residual dark oil. This is taken up in acetone and treated with Norite C-190-N (activated carbon) to give 14.40 g. of a thick orange oil. This is converted to methyl ester by heating at reflux in 17 ml. of methanol. 40 ml. of ethylene dichloride and 2 ml. of concentrated sulfuric acid for 3.5 hours. The mixture is diluted with 165 ml. of methylene chloride, washed with water, 10% sodium bicarbonate solution and water, and dried ($Na_2SO_4$). The residual colored oil remaining after removing the solvent weighs 12.8 gm. Ten grams of this material in a small volume of acetone is chromatographed over 1 kg. of silica gel wet packed with 10% acetone: Skellysolve B hydrocarbons. The column is eluted in cuts of 200 ml. each with the same solvent mixture. The product is eluted in cuts 13–23 as determined by tlc and ir examination: yield 7.27 g. of solid. A sample is crystallized from ether-pentane; m.p. 83°–86°.

Analysis calcd. for: $C_{16}H_{13}NO_4$; C, 67.36; H, 5.30; N, 4.91; Found: C, 67.26; H, 5.37; N. 4.86 d. Product

A mixture of 4.02 g. of the above-described methyl ester, 500 ml. of methanol, and 20 ml. of 10% sodium hydroxide solution is heated at reflux under nitrogen for 45 minutes. The mixture is concentrated on a rotary evaporator to remove methanol, diluted with water, acidified with hydrochloric acid and allowed to stand until the product solidifies. After chilling, the solid is recovered, washed with water and dried, yield 3.71 g., m.p. 116°–119°. When recrystallized from methylene chloride-Skellysolve B, the solid melts at 117°–120°.

Analysis Calcd. for: $C_{15}H_{13}NO_4$; C, 66.41; H, 4.83; N, 5.16; Found: C, 65.98 H, 4.90; N, 4.98

This compound is high in anti-thrombotic activity and low in anti-inflammatory activity.

EXAMPLE 4

A lot of 10,000 tablets each containing 50 mg. of 2-(2-fluoro-2'-nitro-4-biphenylyl)propionic acid is prepared from the following types and amounts of ingredients:

| 2-(2-fluoro-2'-nitro-4-biphenylyl)-propionic acid | 500 Gm. |
|---|---|
| Dicalcium phosphate | 3,000 Gm. |
| Methylcellulose, U.S.P. (15 cps) | 120 Gm. |
| Talc | 300 Gm. |
| Corn starch | 400 Gm. |
| Magnesium stearate | 25 Gm. |

The dicalcium phosphate is mixed well, granulated with 7.5 percent solution of methylcellulose in water, passed through a No. 8 screen and dried carefully. The dried granules are passed through a No. 12 screen, mixed thoroughly with the talc, starch and magnesium stearate and compressed into tablets.

The tablets are useful in treating arthritis at a dose of one tablet three times a day.

EXAMPLE 5

One thousand two-piece hard gelatin capsules, each containing 25 mg. of 2-(2-fluoro-2'-amino-4-biphenylyl)propionic acid are prepared from the following types and amounts of ingredients:

| 2-(2-fluoro-2'-amino-4-biphenylyl)-propionic acid | 25 Gm. |
|---|---|
| Talc | 50 Gm. |
| Magnesium stearate | 0.5 Gm. |

The ingredients are mixed well and filled into capsules of the proper size.

Capsules so prepared are useful in preventing further coronary infarcts at a dose of 2 capsules daily to a patient recovering from a coronary infarct.

EXAMPLE 6

One thousand tablets, each containing 30 mg. of 2-(2'-nitro-4-biphenylyl)propionic acid are prepared from the following types and amounts of ingredients:

| 2-(2'-nitro-4-biphenylyl)-propionic acid | 30 Gm. |
|---|---|
| Microcrystalline cellulose NF | 40 Gm. |
| Starch | 5 Gm. |
| Magnesium stearate powder | 0.5 Gm. |

The ingredients are screened, blended together and pressed into tablets.

The tablets are useful in protecting against transient cerebral ischemic attacks at a dose of one tablet daily.

EXAMPLE 7

A sterile preparation suitable for intramuscular injection and containing 15 mg. of 2-(2-fluoro-2'-amino-4-biphenylyl)propionic acid in each milliliter is prepared from the following ingredients:

| 2-(2-fluoro-2'-amino-4-biphenylyl)-propionic acid | 22.5 Gm. |
|---|---|
| Benzyl benzoate | 300 ml. |
| Methylparaben | 2.3 Gm. |
| Propylparaben | 0.75 Gm. |
| Peanut oil, q.s. | 1.5 l. |

One milliliter of this sterile preparation is injected for prophylactic treatment of potential thrombosis prior to surgery.

EXAMPLE 8

D(+)2-(2-Fluoro-2'-nitro-4-biphenylyl)propionic acid

A solution of racemic 2-(2-fluoro-2'-nitro-4-biphenylyl)propionic acid (2.89 gm.) in chloroform (25 ml.) treated with d-(+)-α-methylbenzylamine (1.21 ml.) and the mixture heated at reflux for fifteen minutes. The solvent is removed on the rotary evaporator and the solid residue recrystallized three times from methanol-water (1:1), giving crystals of m.p. 176°–183°. This salt is treated with dilute hydrochloric acid and the resulting mixture extracted three times with ether. The ether solution is washed three times with water and then dried over sodium sulfate. The residue obtained by evaporation is recrystallized from ether-pentane, giving 0.71 gm. of product, m.p. 133°–134°, $[\alpha]_D$ − 30° in ethanol.

The combined filtrates from the three recrystallizations from methanol water above are allowed to evaporate. The residue is treated with dilute hydrochloric acid and extracted with ether. The free acid so obtained (1.90 gm.) is reacted with 1-(−)-α-methylbenzylamine and crystallized from chloroform, m.p. 174°–178°. One further recrystallization from chloroform gives salt, m.p. 174°–178°. Free acid, obtained as described above, is recrystallized from ether pentane, giving 0.70 gm. of product, m.p. 133°–135° $[\alpha]_D$ + 31° in ethanol.

We claim:

1. A pharmaceutical composition which comprises an antiinflammatory effective amount of a compound of the formula

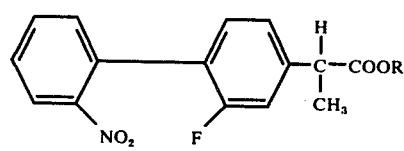

wherein R is hydrogen or alkyl of one to six carbon atoms, inclusive, in association with a pharmaceutical carrier.

2. A composition in accordance with claim 1 suitable for oral or parenteral use.

3. A composition in accordance with claim 2 wherein R is hydrogen.

4. A pharmaceutical composition which comprises an anti-thrombotic effective amount of a compound of the formula

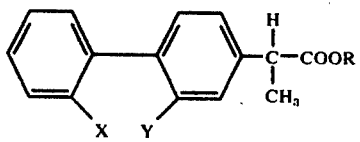

wherein X is nitro or amino and when X is nitro, Y is hydrogen and when X is amino, Y is fluoro, R is hydrogen or alkyl of one to six carbon atoms, inclusive, in association with a pharmaceutical carrier.

5. A composition in accordance with claim 4 suitable for oral or parenteral use.

6. A composition in accordance with claim 5 wherein R is hydrogen.

7. A method for obtaining an anti-inflammatory effect in a mammal which comprises administering to a mammal an anti-inflammatory effective amount of compound

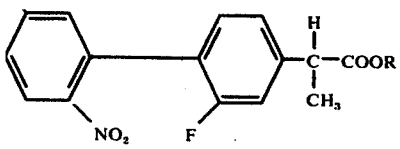

wherein R is selected from the group consisting of hydrogen and alkyl of from one to six carbon atoms, inclusive, in association with a pharmaceutical carrier.

8. A method in accordance with claim 7 wherein the administration is oral or parenteral.

9. A method for obtaining an anti-thrombotic effect in a mammal in need thereof which comprises administering to a mammal an anti-thrombotic effective amount of a compound selected from the group consisting of

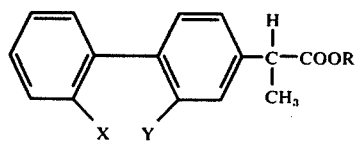

wherein X is selected from the group consisting of nitro and amino Y is selected from the group consisting of hydrogen and fluoro with the proviso that when X is nitro, Y is hydrogen and when X is amino, Y is fluoro, and R is selected from the group consisting of hydrogen and alkyl from one to six carbon atoms, inclusive, in association with a pharmaceutical carrier.

10. A method in accordance with claim 9 wherein the administration is oral or parenteral.

11. A method in accordance with claim 8 wherein R is hydrogen.

12. A method in accordance with claim 10 wherein R is hydrogen.

* * * * *